(12) United States Patent
Uhr et al.

(10) Patent No.: US 9,296,878 B2
(45) Date of Patent: Mar. 29, 2016

(54) FUNGICIDE FORMULATIONS FOR PLASTICIZED PVC

(71) Applicant: LANXESS Deutschland GmbH, Cologne (DE)

(72) Inventors: Hermann Uhr, Leverkusen (DE); Andreas Boettcher, Cologne (DE); Thomas Jaetsch, Cologne (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 14/388,263

(22) PCT Filed: Mar. 26, 2013

(86) PCT No.: PCT/EP2013/056407
§ 371 (c)(1),
(2) Date: Sep. 26, 2014

(87) PCT Pub. No.: WO2013/144147
PCT Pub. Date: Oct. 3, 2013

(65) Prior Publication Data
US 2015/0203660 A1 Jul. 23, 2015

(30) Foreign Application Priority Data
Mar. 28, 2012 (EP) .................................. 12161923
Apr. 23, 2012 (EP) .................................. 12165125

(51) Int. Cl.
| | |
|---|---|
| *C09D 5/16* | (2006.01) |
| *C08K 5/47* | (2006.01) |
| *C08K 5/00* | (2006.01) |
| *A01N 47/12* | (2006.01) |
| *C08K 5/205* | (2006.01) |
| *C09D 5/14* | (2006.01) |
| *C09D 127/06* | (2006.01) |
| *C08K 5/12* | (2006.01) |
| *C08K 5/1515* | (2006.01) |
| *A01G 9/02* | (2006.01) |

(52) U.S. Cl.
CPC . *C08K 5/47* (2013.01); *A01N 47/12* (2013.01); *C08K 5/0016* (2013.01); *C08K 5/0058* (2013.01); *C08K 5/12* (2013.01); *C08K 5/1515* (2013.01); *C08K 5/205* (2013.01); *C09D 5/14* (2013.01); *C09D 127/06* (2013.01)

(58) Field of Classification Search
CPC ......... C09D 5/14; C09D 127/06; C08K 5/205
USPC ........................... 523/122; 514/259, 365, 478
See application file for complete search history.

(56) References Cited

U.S. PATENT DOCUMENTS

| | | | |
|---|---|---|---|
| 4,276,211 A | 6/1981 | Singer et al. | |
| 4,297,258 A | 10/1981 | Long, Jr. | |
| 4,552,885 A | 11/1985 | Gabriele et al. | |
| 5,955,483 A | 9/1999 | Gaglani et al. | |
| 6,059,991 A | 5/2000 | Gaglani et al. | |
| 6,136,856 A | 10/2000 | Savage et al. | |
| 6,140,370 A | 10/2000 | Gaglani et al. | |
| 2007/0072850 A1* | 3/2007 | Chou et al. | 514/227.5 |
| 2009/0036555 A1 | 2/2009 | Uhr | |
| 2009/0269379 A1 | 10/2009 | Herbst | |
| 2013/0310428 A1 | 1/2013 | Joseph et al. | |
| 2013/0096227 A1 | 4/2013 | Cornish et al. | |

FOREIGN PATENT DOCUMENTS

| | | |
|---|---|---|
| DE | 10146189 A1 | 11/2002 |
| JP | 2225548 A2 | 9/1990 |
| JP | 8059937 A2 | 3/1996 |
| WO | 9943206 A1 | 9/1999 |
| WO | WO 2006138147 * | 12/2006 |
| WO | 2007101549 A1 | 9/2007 |

OTHER PUBLICATIONS

Dylingowski et al., Paulus, "Microbial degradation of plastics", Directory of Microbicides for the Protection of Materials, 2005, Springer, Berlin, Germany, ISBN 1-4020-2817-2, pp. 325-345.
International Search Report from International Application PCT/EP2013/056407, Sep. 5, 2013, three pages.
European Search Report from European Application No. 12161923, dated Nov. 21, 2012, two pages.

* cited by examiner

*Primary Examiner* — Terressa Boykin

(57) ABSTRACT

The invention relates to stable compositions for providing PVC with fungicidal properties. Said stable compositions contain at least one thiabendazole as an active substance, at least one plasticizer for PVC, at least one thixotropic agent, and, optionally, other fungicidal agents. The invention also relates to methods for producing said formulations and the uses thereof for preventing PVC from being infested and destroyed by microorganisms. The invention further relates to mildew-resistant PVC materials provided with the compositions of the invention.

18 Claims, No Drawings

FUNGICIDE FORMULATIONS FOR PLASTICIZED PVC

The present invention relates to stable compositions for the fungicidal equipment of PVC comprising at least thiabendazole as active compound, at least one plasticizer for PVC, at least one thixotropic agent and optionally other fungicidal active ingredients, and also to methods for preparing these formulations and to uses thereof for the protection of PVC against attack and destruction by microorganisms. Moreover, the invention relates to mold-resistant PVC materials equipped with the compositions according to the invention.

Since the first synthetic polymers were introduced in the 19th century, attack and degradation of polymers by microorganisms such as, for example, fungi has played a major role. The tendency to be attacked and possibly decomposed by microorganisms depends strongly on the structure of the polymers and the additives used. Flexible polyvinyl chloride, which is used, for example, for films for swimming pools, ponds and reservoirs, for textiles, shower curtains, floor seals, floor pads and floor covers, seat covers, flexible seals for refrigerators and washing machines, seals used for roofing, etc., is particularly susceptible to attack by microorganisms owing to its high proportion of plasticizers and other additives. For protection against microorganisms, soft PVC is therefore equipped with antimicrobial agents. Currently, a large proportion is still equipped with the toxicologically highly questionable 10'-oxybisphenoxyarsine (OBPA). As alternatives, use is increasingly made of 2-n-octyl-4-isothiazolin-3-one (OIT) or 4,5-dichloro-2-n-octyl-4-isothiazolin-3-one (DCOIT); however, owing to their highly sensitizing properties they are also both fraught with problems. (W. Paulus, Directory of microbicides for the protection of materials; Springer 2005, pp. 325-345; ISBN 1-4020-2817-2).

By virtue of its favorable toxicological properties, thiabendazole is an ideal fungicide for equipping plastics such as, for example, PVC.

The use of thiabendazole and compositions of thiabendazole with other fungicides for antifungal equipment of soft PVC have already been described in numerous patent applications and publications.

JP 08059937 describes antibacterially and antifungally equipped PVC films comprising, for example, thiabendazole as fungicidally active compound.

JP 02225548 claims thiazolyl derivatives including thiabendazole for protecting vinyl chloride polymers against mold.

Borgmann-Strahsen, R.; Bessems, E. Kunststoffe 84 (1994) 158-162 describes compositions of thiabendazole and n-octylisothiazolinone ensuring good protection of PVC against attack by mold.

WO 2008075014 describes antifungal formulations comprising a plasticizer, and articles prepared from or coated with these formulations. The fungicides are fludioxonil and/or difenoconazole, with thiabendazole also being mentioned as optional mixing partner.

DE 10146189 claims mold-free PVC compositions for refrigerator door seals, which compositions comprise, as fungicidal component, carbendazim, thiabendazole, tebuconazole or zinc pyrithione.

Mixtures of thiabendazole and plasticizers are frequently suspensions or dispersions since thiabendazole is, if at all, only poorly soluble in conventional plasticizers. In these suspensions, thiabendazole tends to agglomeration and sedimentation. As a result, corresponding compositions can no longer be uniformly incorporated into a polymer without further technical expenditure.

Accordingly, it was an object of the present invention to prepare a sedimentation- and storage-stable formulation of thiabendazole and optionally other fungicides in plasticizers which can be incorporated into the PVC without any problems.

This object is advantageously achieved by a composition comprising thiabendazole, its salts or acid addition compounds, at least one plasticizer and at least one thixotropic agent.

Accordingly, the invention provides compositions comprising thiabendazole, its salts or acid addition compounds, at least one plasticizer and at least one thixotropic agent.

For the purpose of the invention, compositions are mixtures which may be present in various states. The compositions according to the invention are preferably dispersions.

The plasticizers can be any substances used to make plastics, preferably thermoplastic polymers and in particular PVC, soft and flexible.

These are preferably phthalates, such as, in particular, diethylhexyl phthalate (DEHP), dibutyl phthalate (BBP), diisononyl phthalate (DINP), diisodecyl phthalate (DIDP), diisooctyl phthalate (DNOP), diisobutyl phthalate (DIBP), diisohexyl phthalate, diisoheptyl phthalate, di-n-octyl phthalate, diisoundecyl phthalate, diisotredecyl phthalate; adipates such as, in particular, diethylhexyl adipate (DEHA), diisooctyl adipate, diisononyl adipate, polyesters of adipic acid or glutaric acid such as, in particular, Ultramoll® IV from Lanxess Deutschland GmbH; trialkyl esters of citric acid or acetylated trialkyl esters of citric acid such as, in particular, acetyl tributyl citrate (ATBC); esters of trimellitic acid such as, in particular, tri(2-ethylhexyl)trimellitate, tri(isooctyl)trimellitate, tri(isononyl)trimellitate; 1,2-dicyclohexyl-based plasticizers such as, in particular, 1,2-cyclohexanedicarboxylic acid nonyl ester (Hexamoll®, DINCH); alkylsulfonic esters of phenol such as, in particular, Mesamoll® from Lanxess Deutschland GmbH (CAS-No. 091082-17-6); acetylated mono- and diglycerides; benzoic acid diesters, in particular of dialkylene glycols, such as, in particular, dipropylene glycol dibenzoate, or isononyl benzoate; trimethylolpropane esters such as, in particular, trimethylolpropane benzoate 2-ethylhexanoate mixtures; dialkyl esters of terephthalic acid such as, in particular, di-2-ethylhexyl terephthalate.

Also suitable for use as plasticizers are epoxidized fatty acids, epoxidized fatty acid esters and epoxidized fatty acid glycerides. These epoxidized fatty acids, epoxidized fatty acid esters and epoxidized fatty acid glycerides can be prepared by processes known from the prior art such as the epoxidation of the corresponding fatty acids, fatty acid esters and fatty acid glycerides, for example, or by esterification of the epoxidized fatty acids with mono-, di- or trihydric alcohols such as, in particular, glycerol, or they represent naturally epoxidized fatty acids such as, in particular, 12-(R),13-(S)-epoxy-9-cis-octadecenoic acid (vernolic acid).

Suitable for use as epoxidized fatty acids are in particular the epoxides of monounsaturated fatty acids such as (10Z)-undeca-10-enoic acid, (9Z)-tetradeca-9-enoic acid, (9Z)-hexadeca-9-enoic acid, (6Z)-octadeca-6-enoic acid, (9Z)-octadeca-9-enoic acid, (9E)-octadeca-9-enoic acid, (11E)-octadeca-11-enoic acid, (9Z)-eicosa-9-enoic acid, (11Z)-eicosa-1-enoic acid, (11Z)-docosa-11-enoic acid, (13Z)-docosa-13-enoic acid or (15Z)-tetracosa-15-enoic acid, or of diunsaturated fatty acids such as, in particular, (9Z,12Z)-octadeca-9,12-dienoic acid, 9-cis-octadecenoic acid or 12-hydroxy-9-cis-octadecenoic acid or of triunsaturated fatty acids such as, in particular, (6Z,9Z,12Z)-octadeca-6,9,12-trienoic acid, (9Z,12Z,15Z)-octadeca-9,12,15-trienoic acid, (8E,10E,12Z)-octadeca-8,10,12-trienoic acid, (9Z,11E,13Z)-octadeca-9,11,13-trienoic acid, (9Z,11E,13E)-octadeca-9,11,13-trienoic acid, (9E,11E,13E)-octadeca-9,11,13-trienoic acid or polyunsaturated fatty acids such as, in particular, (5Z,8Z,11Z,14Z)-eicosa-5,8,11,14-tetraenoic acid, (5Z,8Z,11Z,14Z,17Z)-eicosa-5,8,11,14,17-pentaenoic acid, (7Z,10Z,13Z,16Z,19Z)-docosa-7,10,13,16,19-pentaenoic acid, (4Z,7Z,10Z,13Z,16Z,19Z)-docosa-4,7,10,13,16,19-hexaenoic acid.

If the plasticizers used are epoxides, particular preference is given to triglycerides of epoxidized fatty acids having a carbon length of from 17 to 23 carbon atoms and at least one epoxide group.

With very particular preference, the plasticizers used may also be the following epoxides: linseed oil epoxidates, vernonia oil epoxidates, sunflower oil epoxidates, castor oil epoxidates and soybean oil epoxidates, such as, in particular, epoxidized soybean oil (CAS No. 8013-07-8).

Here, the plasticizers can either be employed as a single component, or else also consist of compositions of a plurality of plasticizers.

The thixotropic agents are generally all substances capable of stabilizing dispersions of thiabendazole and optionally other fungicides in plasticizers and thus prevent sedimentation of the active compounds. In the compositions according to the invention, the thixotropic agents form dispersions having a viscosity at 20° C. of from 100 to 3000 mPas, preferably from 150 to 2500 mPas, measured at an applied shear force of 30 s$^{-1}$.

The thixotropic agents are preferably inorganic thixotropic agents such as modified sheet silicates, fumed silica or precipitated silica or organic thixotropic agents such as castor oil derivatives or mono-, di- or triglycerides of ricinoleic acid derivatives, in particular mono-, di- or triglycerides of (12R)-cis-12-hydroxyoctadec-9-enoic acid, (9Z,12R)-12-hydroxyoctadec-9-enoic acid or 12-hydroxyoctadecanoic acid, esters or amides of ricinoleic acid or their salts, modified polyamides or fatty acid amides, modified polyamide waxes such as, in particular, Luvotix® HP from Lehmann & Voss, Hamburg, Germany, polyolefins with thixotropic action such as, in particular, Luvotix® P25x from Lehmann & Voss, Hamburg, Germany, urea derivatives or specifically modified alkyd resins or compositions thereof.

The thixotropic agents are particularly preferably castor oil derivatives such as, for example, hydrogenated castor oil, sulfated castor oil (CAS 8002-33-3), castor oil derivatized with polyamides or fatty acid amides, in particular Luvotix® HT from Lehmann & Voss, Hamburg, Germany, inorganically modified castor oil, silicate-modified castor oil such as, in particular, Luvotix® ZR 50 from Lehmann & Voss, Hamburg, Germany, modified polyamides such as Rilanit® plus from Cognis, modified polyamide waxes such as, in particular, Luvotix® HP from Lehmann & Voss, Hamburg, Germany, polyolefins with thixotropic action such as, in particular, Luvotix® P25x or Luvotix® P50 from Lehmann & Voss, Hamburg, Germany, alkyd resins with thixotropic action having, for example, urea structures or being urethanized, or triglycerides of ricinoleic acid derivatives, in particular triglycerides of (12R)-cis-12-hydroxyoctadec-9-enoic acid, (9Z,12R)-12-hydroxyoctadec-9-enoic acid or 12-hydroxyoctadecanoic acid, esters or amides of ricinoleic acid or their salts. The triglycerides of ricinoleic acid derivatives, of ricinoleic acid or of hydrogenated ricinoleic acid (12-hydroxyoctadecanoic acid), their esters or their amides and salts thereof can be employed in compositions which may optionally comprise further saturated, unsaturated, branched or straight-chain fatty acids. Preference is given to using the triglycerides of ricinoleic acid derivatives, of ricinoleic acid or of hydrogenated ricinoleic acid (12-hydroxyoctadecanoic acid), their esters or their amides and salts thereof in the compositions according to the invention.

With very particular preference, the castor oil derivative employed is hydrogenated castor oil (CAS No. 8001-78-3) as contained, for example, in Luvotix® R from Lehmann & Voss, Hamburg, Germany.

It is also possible to use other thixotropic agents or compositions of thixotropic agents. The thixotropic agents that may be employed are generally commercially available and are usually also employed in solvent-based paints to prevent settling of the pigments.

Thiabendazole is 2-(4-thiazolyl)-1H-benzimidazole.

In addition to thiabendazole, the compositions may optionally also comprise one or more further fungicidally active compounds. This may improve mold-resistance of the PVC even more. Frequently, synergistic effects are additionally also observed.

In general, all fungicides acting against mold fungi may be employed for this purpose. Here, too, it is possible to employ compositions to improve the activity even more.

The fungicides are preferably
triazoles such as:
azaconazole, azocyclotin, bitertanol, bromuconazole, cyproconazole, diclobutrazole, difenoconazole, diniconazole, epoxiconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazole, penconazole, propioconazole, prothioconazole, simeoconazole, (±)-cis-1-(4-chlorophenyl)-2-(1H-1,2,4-triazol-1-yl)cycloheptanol, 2-(1-tert-butyl)-1-(2-chlorophenyl)-3-(1,2,4-triazol-1-yl) propan-2-ol, tebuconazole, tetraconazole, triadimefon, triadimenol, triapenthenol, triflumizole, triticonazole, uniconazole and their metal salts and acid adducts;
imidazoles such as:
clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chloro-phenoxy)-3,3-dimethylbutan-2-one, and their metal salts and acid adducts;
pyridines and pyrimidines such as:
ancymidol, buthiobate, fenarimol, mepanipyrin, nuarimol, pyroxyfur, triamirol;
succinate dehydrogenase inhibitors such as:
benodanil, carboxim, carboxim sulfoxide, cyclafluramid, fenfuram, flutanil, furcarbanil, furmecyclox, mebenil, mepronil, methfuroxam, metsulfovax, nicobifen, pyrocarbolid, oxycarboxin, Shirlan, Seedvax;
naphthalene derivatives such as:
terbinafine, naftifine, butenafine, 3-chloro-7-(2-aza-2,7,7-trimethyloct-3-en-5-yne);
sulfenamides such as:
dichlorfluanid, tolylfluanid, folpet, fluorofolpet, captan, captofol;
benzimidazoles such as:
carbendazim, benomyl, fuberidazole or their salts;
morpholine derivatives such as:
aldimorph, dimethomorph, dodemorph, falimorph, fenpropidin, fenpropimorph, tridemorph, trimorphamid and their arylsulfonate salts such as, for example, p-toluenesulfonic acid and p-dodecylphenylsulfonic acid;

benzothiazoles such as:
2-mercaptobenzothiazole;
benzothiophene dioxides such as:
N-cyclohexyl-benzo[b]thiophenecarboxamide S,S-dioxide;
benzamides such as:
2,6-dichloro-N-(4-trifluoromethylbenzyl)benzamide, tecloftalam;
boron compounds such as:
boric acid, boric esters, borax;
isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octylisothiazolin-3-one, 4,5-trimethyleneiso-thiazolinone, 4,5-benzisothiazolinone;
thiocyanates such as:
thiocyanatomethylthiobenzothiazole, methylenebisthiocyanate;
quaternary ammonium compounds and guanidines such as:
benzalkonium chloride, benzyldimethyltetradecylammonium chloride, benzyldimethyl-dodecylammonium chloride, dichlorobenzyldimethylalkylammonium chloride, didecyldimethyl-ammonium chloride, dioctyldimethylammonium chloride. N-hexadecyltrimethylammonium chloride, 1-hexadecylpyridinium chloride, iminoctadine tris(albesilate);
iodine derivatives such as:
diiodomethyl-p-tolylsulfone, 3-iodo-2-propynyl alcohol, 4-chlorophenyl 3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate;
phenols such as:
tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, methyl p-hydroxybenzoate, ethyl p-hydroxybenzoate, propyl p-hydroxybenzoate, butyl p-hydroxybenzoate, octyl p-hydroxybenzoate, 4-(2-tert-butyl-4-methylphenoxy)phenol, 4-(2-isopropyl-4-methylphenoxy)phenol, 4-(2,4-dimethylphenoxyl)phenol and their alkali metal salts and alkaline earth metal salts;
pyridines such as:
1-hydroxy-2-pyrdinethione (and their Cu, Na, Fe, Mn, Zn salts), tetrachloro-4-methylsulfonylpyridine, pyrimethanol, mepanipyrim, dipyrithione, 1-hydroxy-4-methyl-6-(2,4,4-trimethylpentyl)-2(1H)-pyridine;
methoxyacrylates or similar compounds such as:
azoxystrobin, dimoxystrobin, fluoxastrobin, kresoxim-methyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene]amino]oxy]methyl]phenyl]-3H-1,2,4-triazol-3-one (CAS No. 185336-79-2);
oxides such as:
oxides of the metals tin, copper and zinc, such as, for example, tributyltin oxide, $Cu_2O$, CuO, ZnO;
dithiocarbamates such as:
cufraneb, ferban, potassium N-hydroxymethyl-N'-methyldithiocarbamate, sodium dimethyldithiocarbamate, potassium dimethyldithiocarbamate, mancozeb, maneb, metam, metiram, thiram, zineb, ziram;
nitriles such as:
2,4,5,6-tetrachloroisophthalonitrile, disodium cyanodithioimidocarbamate;
quinolines such as:
8-hydroxyquinoline and the copper salts thereof;
Ag-, Zn- or Cu-containing zeolites on their own or encapsulated in polymeric materials.

Very particularly preferably, the fungicides are azaconazole, bromuconazole, cyproconazole, dichlobutrazole, diniconazole, difenconazole, hexaconazole, metaconazole, penconazole, propiconazole, tebuconazole, azoxystrobin, fludioxonil, dichlofluanid, tolylfluanid, fluorfolpet, methfuroxam, carboxin, fenpiclonil, butenafin, imazalil, N-octylisothiazolin-3-one, dichloro-N-octylisothiazolinone, mercaptobenzothiazole, thiocyanatomethyl-thiobenzothiazole. N-butyl-benzisothiazolinone, 1-hydroxy-2-pyridinthione (and their Cu, Na, Fe, Mn, Zn salts), tetrachloro-4-methylsulfonylpyridine, 3-iodo-2-propynyl n-butylcarbamate, diiodomethyl-p-tolylsulfone, bethoxazin, 2,4,5,6-tetrachloroisophthalodinitrile and carbendazim.

Algicides to prevent the growth of algae on the PVC surfaces, or agents which, by virtue of their unpleasant or bitter taste, prevent, for example, martens biting into flexible car parts/seals/isolations may also be optionally added.

If an iodine-containing compound is used as additional fungicide, the compositions, in particular dispersions or suspensions, in combination with thiabendazole in storage are, in particular at elevated temperatures, not stable. The iodine-containing fungicides are chemically degraded even after a relatively short time. This is different from the transition metal- or light-induced decomposition of the iodine-containing fungicides. Here, the active compound thiabendazole causes the decomposition.

Iodine-containing fungicides which may be mentioned are, for example, N—($C_1$-$C_{12}$)-alkyl-iodotetrazoles, N—($C_6$-$C_{15}$)-aryl-iodotetrazoles. N—($C_6$-$C_{15}$)-arylalkyl-iodotetrazoles, diiodomethyl-p-tolylsulfone, diiodomethyl-p-chlorophenylsulfone, 3-bromo-2,3-diiodo-2-propenyl alcohol, 2,3,3-triiodoallyl alcohol, 4-chloro-2-(2-chloro-2-methylpropy))-5-[(6-iodo-3-pyridinyl)methoxy]-3(2H)-pyridazinone (CAS-RN: 120955-77-3), iodfenfos, 3-iodo-2-propynyl 2,4,5-trichlorophenyl ether, 3-iodo-2-propynyl 4-chlorophenyl formal (IPCF), N-iodopropargyloxycarbonyl-alanine, N-iodopropargyloxycarbonyl-alanine ethyl ester, 3-(3-iodopropargyl)-benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl) hexyldicarbamate, diiodomethyl-p-tolylsulfone, 3-iodo-2-propynyloxyethanol ethylcarbamate, 3-iodo-2-propynyloxyethanol phenylcarbamate, 3-iodo-2-propynyl thioxo thioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

Preferred iodine-containing fungicides are 3-iodo-2-propynyl 2,4,5-trichlorophenyl ether, 3-iodo-2-propynyl 4-chlorophenyl formal (IPCF), N-iodopropargyloxycarbonyl-alanine, N-iodopropargyloxyearbonyl-alanine ethyl ester, 3-(3-iodopropargyl)-benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl) hexyldicarbamate, diiodomethyl-p-tolylsulfone, 3-iodo-2-propynyloxyethanol ethylcarbamate, 3-iodo-2-propynyloxyethanol phenylcarbamate, 3-iodo-2-propynyl thioxo thioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

Particularly preferred iodine-containing fungicides are 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl) hexyldicarbamate, 3-iodo-2-propynyloxyethanol ethylcarbamate, 3-iodo-2-propynyl-oxyethanol phenylcarbamate, 3-iodo-2-propynyl thioxo thioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate, with 3-iodo-2-propynyl butylcarbamate (IPBC) and diiodomethyl-p-tolylsulfone being even more preferred.

It has now been found that a composition comprising thiabendazole, its salts or acid addition compounds, at least one plasticizer and at least one thixotropic agent and at least one iodine-containing fungicide and at least one epoxide counteracts decomposition of the IPBC and stabilizes the composition.

Furthermore, the invention embraces a composition comprising thiabendazole, its salts or acid addition compounds, at least one iodine-containing fungicide and at least one epoxide.

Methods for preventing the degradation of iodopropargyl compounds in transition metal-containing solvent based alkyd resin containing paints and for stabilizing them in this manner are known from the prior art. Here, the presence of transition metals is causing the decomposition of the iodopropargyl compounds. Thus, it is known to add, for example, chelating agents (WO 98/22543 A), organic epoxides (WO 00/16628 A, 2-(2-hydroxyphenyl)benzotriazoles (W) 2007/028527 A) or azole compounds (WO 2007/101549 A).

Also known are methods for reducing the light-induced discoloration of iodoprogargyl compounds in water-based paints by employing epoxides (U.S. Pat. No. 4,276,211, U.S. Pat. No. 4,297,258), optionally in combination with UV absorbers (WO 99/29176 A) or benzylidene camphor derivatives (U.S. Pat. No. 6,472,424), tetraalkylpiperidine compounds and/or UV absorbers (EP 0 083 308 A).

In general, these can be any compounds containing one or more epoxide groups in the molecule and otherwise compatible with thiabendazole, the other fungicides and auxiliaries and having a boiling point above the processing temperature of the PVC. Hereinbelow, compounds containing one or more epoxide groups in the molecule are referred to as "epoxides". The epoxides which can be employed as stabilizers in the context of the invention generally have a boiling point above 180° C. and preferably a boiling point above 200° C.

The epoxides which may preferably be used for stabilization include the following compounds:

-continued where
R$^1$ represents C$_1$-C$_{20}$-alkyl
R$^2$ represents H, alkyl, substituted alkyl,
R$^3$ represents halogen,
R$^4$ represents C$_1$-C$_{20}$-alkyl and
R$^5$ represents H, C$_1$-C$_{20}$-alkyl, preferably methyl or ethyl,
and also epoxides such as
1-Methyl-4-(1-methylethenyl)-7-oxabicyclo[4.1.0]heptane (CAS-RN 1195-92-2), 1-Methyl-4-(2-methyl-2-oxiranyl)-7-oxabicyclo[4.1.0]heptane (CAS-RN 96-08-2), 2,2'-[1,4-cyclohexanediylbis(methyleneoxymethylene)]bis-oxirane (CAS-RN 14228-35-5), 2,2'-[(1-methylethylidene)bis(4,1-phenyleneoxymethylene)]bis-oxirane (CAS-RN 1675-54-3), 3-(2-oxiranyl)-7-oxabicyclo[4.1.0]heptane (CAS-RN 106-87-6), 7-oxabicyclo[4.1.0]hept-3-ylmethyl-7-oxabicyclo[4.1.0]heptane-3-carboxylic acid ester (CAS-RN 2386-87-0), 1,6-bis(7-oxabicyclo[4.1.0]hept-3-ylmethyl)hexanedioic acid ester (CAS-RN 3130-19-6) and further epoxides which are prepared by the epoxidation of double bonds in unsaturated fatty acids, fatty acid esters and fatty acid glycerides. The epoxides of the unsaturated fatty acids, fatty acid esters and fatty acid glycerides which can be used for stabilization may simultaneously also be used as plasticizers. However, in their role as stabilizers, they are effective at considerably lower concentrations.

Accordingly, the epoxidized fatty acids, epoxidized fatty acid esters or epoxidized fatty acid glycerides which can be used as plasticizers may also be used as stabilizers. With preference, the epoxides which can be used as plasticizers are also used as stabilizers.

The epoxidized fatty acid esters or epoxidized fatty acid glycerides can be prepared by processes known to the person skilled in the art, for example by esterification of the epoxidized fatty acids with mono-, di- or trihydric alcohols such as, in particular, glycerol.

Particularly preferred as epoxides for stabilizing the iodine-containing fungicides are epoxidized fatty acid glycerides, epoxidized fatty acid esters or epoxidized fatty acids whose fatty acids have a carbon length of from 17 to 23 carbon atoms and contain at least one epoxide group.

With very particular preference, the epoxides for stabilization are linseed oil epoxidates, vernonia oil epoxidates, sunflower oil epoxidates and soybean oil epoxidates in particular epoxidized soybean oil (CAS No. 8013-07-8).

If, in the process according to the invention, the plasticizers used are epoxides, it is possible to use additional further epoxides as stabilizers. In this case, it is preferred not to use any additional epoxides as stabilizers.

To improve properties such as temperature sensitivity, UV stability, oxidation stability of the dispersions themselves, the dispersions during incorporation into the PVC and the PVC preparations prepared therefrom even more, it is possible to employ further stabilizers.

The further stabilizers which can optionally be employed may be antioxidants, free radical scavengers or UV absorbers. One or more of these substances may optionally be employed.

Examples of further stabilizers which may be mentioned are:

sterically hindered phenols, such as 2,6-di-tert-butyl-4-methylphenol, 2-tert-butyl-4,6-dimethylphenol, 2,6-di-cyclopentyl-4-methylphenol, 2-(α-methylcyclohexyl)-4,6-dimethylphenol, 2,6-di-octadecyl-4-methylphenol or 2,6-di-tert-butyl-4-methoxymethylphenol, diethyl(3,5-di-tert-buty)-4-hydroxybenzyl)phosphonate, 2,4-dimethyl-6-(1-methylpentadecyl)phenol, 2-methyl-4,6-bis[(octylthio)methyl]phenol, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 2,2'-methylenebis(6-tert-butyl-4-methylphenol), 2,2'-methylenebis-(4-methyl-6-cyclohexylphenol), 2,2'-methylenebis(4,6-di-tert-butylphenol), 2,2'-ethylidenebis(4,6-di-tert-butylphenol), 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 1,1,3-tris(5-tert-butyl-4-hydroxy-2-methylphenyl)butane, 1,3,5-tri(3,5-di-tert-butyl-4-hydroxybenzyl)-2,4,6-trimethylbenzene, isooctyl 3,5-di-tert-butyl-4-hydroxybenzylmercaptoacetate, 1,3,5-tris(3,5-di-tert-butyl-4-hydroxybenzyl) isocyanurate, 1,3,5-tris(4-tert-butyl-3-hydroxy-2,6-ditnethylbenzyl) isocyanurate, 1,3,5-tris[(3,5-di-tert-butyl-4-hydroxyphenyl)propionyloxyethyl]isocyanurate, dioctadecyl 3,5-di-tert-butyl-4-hydroxybenzylphosphonate, calcium monoethyl 3,5-di-tert-butyl-4-hydroxybenzylphosphonate, N,N'-di-(3,5-di-tert-butyl-4-hydroxyphenylpropionyl) hexamethylenediamine, N,N'-di-(3,5-di-tert-butyl-4-hydroxyphenylpropionyl)trimethylenediamine, N,N'-di-(3,5-di-tert-butyl-4-hydroxyphenylpropionyl)hydrazine, 3,9-bis[1,1-dimethyl-2-[(3-tert-butyl-4-hydroxy-5-methylphenyl)propionyloxy]ethyl]-2,4,8,10-tetraoxaspiro[5.5]undecane, bis[3,3-bis(4'-hydroxy-3'-tert-butylphenyl)butanoic acid]ethylene glycol ester, 2,6-bis[[3-(1,1-dimethylethyl)-2-hydroxy-5-methylphenyl]octahydro-4,7-methano-1H-indenyl]-4-methylphenol (=Wingstay L), 2,4-bis(n-octylthio)-6-(3,5-di-tert-butyl-4-hydroxyphenylamino)-s-triazine, N-(4-hydroxyphenyl) octadecaneamide, 2,4-di-tert-butylphenyl 3',5'-di-tert-butyl-4'-hydroxybenzoate, (benzoic acid, 3,5-bis(1,1-dimethylethyl)-4-hydroxy-, hexadecyl ester), 3-hydroxyphenyl benzoate, 2,2'-methylenebis(6-tert-butyl-4-methylphenol)monoacrylate, 2-(1,1-dimethylethyl)-6-[1-[3-(1,1-dimethylethyl)-5-(1,1-dimethylpropyl)-2-hydroxyphenyl]ethyl]-4-(1,1-dimethyl-propyl)phenyl ester, esters of β-(3,5-di-tert-butyl-4-hydroxyphenyl)propionic acid with monohydric or polyhydric alcohols such as, in particular, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide, esters of β-(5-tert-butyl-4-hydroxy-3-methylphenyl)propionic acid with monohydric or polyhydric alcohols such as, in particular, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide.

Hindered amines, such as bis(1,2,2,6,6-pentamethyl-4-piperidyl) 2-(3,5-di-tert-butyl-4-hydroxybenzyl)-2-butyl malonate, bis(2,2,6,6-tetramethyl-4-piperidyl)decanediate, dimethyl succinate-1-(2-hydroxyethyl)-4-hydroxy-2,2,6,6-tetramethylpiperidine copolymer, poly[[6-[(1,1,3,3-tetramethylbutyl)amino]-1,3,5-triazine-2,4-diyl]][(2,2,6,6-tetramethyl-4-piperidyl)imino] hexamethylene[(2,2,6,6-tetramethyl-4-piperidyl)amino]] (CAS No. 71878-19-8), 1,5,8,12-tetrakis[4,6-bis(N-butyl-N-1,2,2,6,6-penta-methyl-4-piperidylamino)-1,3,5-triazin-2-yl]-1,5,8,12-tetraazadodecane (CAS No. 106990-43-6), bis (1,2,2,6,6-pentamethyl-4-piperidyl)decanedioate, bis(1,2,2,6,6-pentamethyl-4-piperidyl) 2-(3,5-di-tert-butyl-4-hydroxybenzyl)-2-butylmalonate, decanedioic acid, bis(2,2,6,6-tetramethyl-4-piperidinyl) ester, reaction products with tert-butyl hydroperoxide and octane (CAS No. 129757-67-1), Chitnasorb 2020 (CAS No. 192268-64-7), poly[[6-morpholino-1,3,5-triazine-2,4-diyl]-[(2,2,6,6-tetramethyl-4-piperidinyl)iminol-1,6-hexanediyl[(2,2,6,6-tetramethyl-4-piperidinyl)-imino]], poly[[6-(4-morpholinyl)-1,3,5-triazine-2,4-diyl][(1,2,2,6,6-pentamethyl-4-piperidinyl)-imino]-1,6-hexanediyl[(1,2,2,6,6-pentamethyl-4-piperidinyl)imino]] (90), 3-dodecyl-1-(2,2,6,6-tetramethyl-4-piperidyl)pyrrolidine-2,5-dione, 3-dodecyl-1-(1,2,2,6,6-pentamethylpiperidin-4-yl)-pyrrolidine-2,5-dione, 4-octadecanoyloxy-2,2,6,6-tetramethylpiperidine, poly[[6-(cyclohexyl-amino)-1,3,5-triazine-2,4-diyl][(2,2,6,6-tetramethyl-4-piperidinyl)imino]-1,6-hexanediyl[(2,2,6,6-tetramethyl-4-piperidinyl)imino]], 1H,4H,5H,8H-2,3a,4a,6,7a,8a-hexaazacyclopenta[def]fluorene-4,8-dione, hexahydro-2,6-bis(2,2,6,6-tetramethyl-4-piperidinyl)-(CAS No. 109423-00-9), N,N'-bis(formyl)-N,N-bis(2,2,6,6-tetramethyl-4-piperidyl)-1,6-hexanediamine, N-(tetramethyl-4-piperidinyl)maleimide-C20-24-α-olefin copolymer (CAS No. 199237-39-3), tetrakis(1,2,2,6,6-pentamethyl-4-piperidyl) 1,2,3,4-butanetetracarboxylate, tetrakis(2,2,6,6-tetramethyl-4-piperidyl) 1,2,3,4-butanetetracarboxylate, 1,2,2,6,6-pentamethyl-4-piperidinyl tridecyl 1,2,3,4-butanetetracarboxylate, (1,2,3,4-butanetetracarboxylic acid, 2,2,6,6-tetramethyl-4-piperidinyl tridecyl ester), (2,4,8,10-tetraoxaspiro[5.5]undecane-3,9-diethanol, β,β,β',β'-tetramethyl-, polymer with 1,2,3,4-butanetetracarboxylic acid) (CAS No. 115055-30-6), 2,2,4,4-tetramethyl-21-oxo-7-oxa-3,20-diazadispiro[5.1.11.2]heneicosane, (7-oxa-3,20-diazadispiro[5.1.11.2]heneicosane-20-propanoic acid, 2,2,4,4-tetramethyl-21-oxo-, tetradecyl ester), (7-oxa-3,20-diazadispiro-[5.1.11.2]heneicosan-21-one, 2,2,4,4-tetramethyl-20-(oxiranylmethyl)-), (propanamide, N-(2,2,6,6-tetramethyl-4-piperidinyl)-3-[(2,2,6,6-tetramethyl-4-piperidinyl)amino]), (1,3 propane-diamine, N,N'''-1,2-ethanediylbis-, polymer with 2,4,6-trichloro-1,3,5-triazine, reaction products with N-butyl-2,2,6,6-tetramethyl-4-piperidinamine) (CAS No. 136504-96-6), 1,1'-ethylene-bis(3,3,5,5-tetramethyl-2-piperazinone), (piperazinone, 1,1',1'''-[1,3,5-triazine-2,4,6-triyltris-[(cyclohexylimino)-2,1-ethanediyl]]tris[3,3,5,5-tetramethyl-), (7-oxa-3,20-diazadispiro[5.1.11.2]-heneicosane-20-propanoic acid, 2,2,4,4-tetramethyl-21-oxo-, dodecyl ester), 1,1-bis(1,2,2,6,6-pentamethyl-4-piperidyloxycarbonyl)-2-(4-methoxyphenyl) ethene, (2-propenoic acid, 2-methyl-, methyl ester, polymer with 2,2,6,6-tetramethyl-4-piperidinyl 2-propenoate) (CAS No. 154636-12-1), (propanamide, 2-methyl-N-(2,2,6,6-tetramethyl-4-piperidinyl)-2-[(2,2,6,6-tetramethyl-4-piperidinyl)amino]-), (D-glucitol, 1,3:2,4-bis-O-(2,2,6,6-tetramethyl-4-piperidinylidene)-) (CAS No. 99473-08-2), N,N'-bis(2,2,6,6-tetramethyl-4-piperidinyl)isophthalamide, 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, 1-(4-tert-butyl-2-butenyl)-4-hydroxy-2,2,6,6-tetramethylpiperidine, 4-stearoyloxy-2,2,6,6-tetramethylpiperidine, 1-ethyl-4-salicyloyl-oxy-2,2,6,6-tetramethylpiperidine, 4-methacryloyloxy-1,2,2,6,6-pentamethylpiperidine, 1,2,2,6,6-pentamethylpiperidin-4-yl P-(3,5-di-tert-butyl-4-hydroxyphenyl)propionate, 1-benzyl- 2,2,6,6-tetramethyl-4-piperidinyl maleate, (di-2,2,6,6-tetramethylpiperidin-4-yl) adipate, (di-2,2,6,6-tetramethylpiperidin-4-yl) sebacate, (di-1,2,3,3,6-tetramethyl-2,6-diethylpiperidin-4-yl) sebacate, (di-1-ally)-2,2,6,6-tetramethylpiperidin-4-yl) phthalate, 1-propargyl-4-β-cyanoethyl-oxy-2,2,6,6-tetramethylpiperidine, 1-acetyl-2,2,6,6-tetramethylpiperidin-4-yl acetate, trimellitic acid tri(2,2,6,6-tetramethylpiperidin-4-yl) ester, 1-acryloyl-4-benzyloxy-2,2,6,6-tetramethylpiperidine, dibutyl-malonic acid di(1,2,2,6,6-pentamethylpiperidin-4-yl) ester, butyl(3,5-di-tert-butyl-4-hydroxybenzyl)malonic acid di(1,2,2,6,6-pentamethylpiperidin-4-yl) ester, dibenzylmalonic acid di(1,2,2,6,6-pentamethylpiperidin-4-yl) ester, dibenzylmalonic acid di(1,2,3,6-tetramethyl-2,6-diethylpiperidin-4-yl) ester, hexane-1',6'-bis(4-carbamoyloxy-1-n-butyl-2,2,6,6-tetramethylpiperidine), toluene-2',4'-bis(4-carbamoyloxy-1-n-propyl-2,2,6,6-tetramethylpiperidine), dimethyl-bis(2,2,6,6-tetramethylpiperidine-4-oxy)silane, phenyl-tris(2,2,6,6-tetramethylpiperidine-4-oxy)silane, tris(1-propyl-2,2,6,6-tetramethylpiperidin-4-yl)phosphite, tris(1-propyl-2,2,6,6-tetramethylpiperidin-4-yl)phosphate, phenyl[bis(1,2,2,6,6-pentamethylpiperidin-4-yl)phosphonate, di(1,2,2,6,6-pentamethylpiperidin-4-yl) sebacate, N,N'-bis(2,2,6,6-tetramethylpiperidin-4-yl)hexamethylene-1,6-diamine, N,N'-bis(2,2,6,6-tetramethylpiperidin-4-yl)hexamethylene-1,6-diacetamide, 1-acetyl-4-(N-cyclohexylacetamido)-2,2,6,6-tetramethylpiperidine, 4-benzylamino-2,2,6,6-tetramethylpiperidine, N,N'-bis(2,2,6,6-tetramethylpiperidin-4-yl)-N,N'-dibutyladipamide, N,N'-bis(2,2,6,6-tetramethylpiperidin-4-yl)-N,N'-dicyclohexyl(2-hydroxypropylene), N,N'-bis(2,2,6,6-tetramethylpiperidin-4-yl)-p-xylylenediamine, 4-(bis-2-hydroxy-ethyl)amino-1,2,2,6,6-pentamethylpiperidine, 4-(3-methyl-4-hydroxy-5-tert-butyl-benzamido)-2,2,6,6-tetramethylpiperidine, 4-methacrylamino-1,2,2,6,6-pentamethylpiperidine, 9-aza-8,8,10,10-tetramethyl-1,5-dioxaspiro[5.5]undecane, 9-aza-8,8,10,10-tetramethyl-3-ethyl-1,5-dioxaspiro[5.5]-undecane, 8-aza-2,7,7,8,9,9-hexamethyl-1,4-dioxaspiro[4.5]decane, 9-aza-3-hydroxymethyl-3-ethyl-8,8,9,10,10-pentamethyl-1-5-dioxaspiro[5.5]undecane, 9-aza-3-ethyl-3-acetoxymethyl-9-acetyl-8,8,10,10-tetramethyl-1,5-dioxaspiro[5.5]undecane, 2,2,6,6-tetramethylpiperidine-4-spiro-2'-(1',3'-dioxane)-5'-spiro-5"-(1",3"-dioxane)-2"'-spiro-4"'-(2"',2"',6"',6"'-tetramethylpiperidine), 3-benzyl-1,3,8-triaza-7,7,9,9-tetramethyl-spiro[4.5]decane-2,4-dione, 3-n-octyl-1,3,8-triaza-7,7,9,9-tetratnethyl-spiro[4.5]decane-2,4-dione, 3-allyl-1,3,8-triaza-1,7,7,9,9-penta-methyl-spiro[4.5]decane-2,4-dione, 3-glycidyl-1,3,8-triaza-7,7,8,9,9-pentamethyl-spiro[4.5]-decane-2,4-dione, 2-isopropyl-7,7,9,9-tetramethyl-1-oxa-3,8-diaza-4-oxyspiro[4.5]decane, 2-butyl-7,7,9,9-tetramethyl-1-oxa-3,8-diaza-4-oxyspiro[4.5]decane, 2-isopropyl-7,7,9,9-tetramethyl-1-oxa-4,8-diaza-oxyspiro[4.5]decane, 2-butyl-7,7,9,9-tetramethyl-1-oxa-4,8-diaza-3-oxyspiro[4.5]decane, bis[β-(2,2,6,6-tetramethylpiperidino)ethyl]sebacate, α-(2,2,6,6-tetramethylpiperidino)acetic acid n-octyl ester, 1,4-bis(2,2,6,6-tetramethylpiperidino)-2-butene, N-hydroxymethyl-N'-2,2,6,6-tetramethylpiperidin-4-ylurea, N-methoxymethyl-N'-2,2,6,6-tetramethylpiperidin-4-ylurea, N-methoxy-methyl-N'-n-dodecyl-N'-2,2,6,6-tetramethylpiperidin-4-ylurea, O-(2,2,6,6-tetramethylpiperidin-4-yl)-N-methoxymethylurethane.

Phosphites and phosphonates, such as
tri(nonylphenyl)phosphite, tris(2,4-di-tert-butylphenyl) phosphite, bis(2,4-di-tert-butylphenyl)pentaerythritol diphosphite, bis(2,6-di-tert-butyl-4-methylphenyl)pentaerythritol diphosphite, 2,2'-methylenebis(4,6-di-tert-butylphenyl) octyl phosphite, tetrakis(2,4-di-tert-butylphenyl)-[1,1'-biphenyl]-4,4'-diylbisphosphonite, 2,2'-ethylidenebis (4,6-di-tert-butylphenyl) fluorophosphite, dioctadecyl pentaerythritol diphosphonite, 2-[[2,4,8,10-tetrakis(1,1-dimethyl-ethyl)dibenzo[d,f][1,3,2]dioxaphosphepin-6-yl]oxy]-N,N-bis[2-[[2,4,8,10-tetrakis(1,1-dimethyl-ethyl)dibenzo[d,f][1,3,2]dioxaphosphepin-6-yl]oxy]ethyl]ethanamine (CAS No. 80410-33-9), bis(2,4-di-tert-butyl-6-methylphenyl)ethyl phosphite, 2,4,6-tri-tert-butylphenyl 2-butyl-2-ethyl-1,3-propanediol phosphite, bis(2,4-dicumylphenyl)pentaerythritol diphosphite, hydroxylamines, such as
amines, bis(hydrogenated tallow alkyl), oxidized,
secondary arylamines, such as
N-(2-naphthyl)-N-phenylamine, 2,2,4-trimethyl-1,2-dihydroquinoline polymer (CAS No. 26780-96-1), N-2-propyl-N'-phenyl-p-phenylenediamine, N-(1-naphthyl)-N-phenylamine, (benzenamine, N-phenyl-, reaction products with 2,4,4-trimethylpentene) (CAS No. 68411-46-1), 4-(1-methyl-1-phenylethyl)-N-[4-(1-methyl-1-phenylethyl)phenyl] aniline.

Lactones and benzofuranones, such as
Irganox HP 136 (CAS No. 181314-48-7)
Thioethers and thioesters, such as
distearyl 3,3-thiodipropionate, dilauryl 3,3'-thiodipropionate, ditetradecyl thiodipropionate, di-n-octadecyl disulfide.

UV absorbers, such as
(methanone, [methylenebis(hydroxymethoxyphenylene]bis[phenyl-), (methanone, [1,6-hexanediylbis[oxy(2-hydroxy-4,1-phenylene)]]bis[phenyl-), 2-benzoyl-5-methoxyphenol, 2,4-dihydroxybenzophenone, 2,2'-dihydroxy-4-methoxybenzophenone, 2-hydroxy-4-octyloxybenzophenone, 2-hydroxy-4-dodecyloxybenzophenone, 2-(2-hydroxy-4-hexyloxyphenyl)-4,6-diphenyl-1,3,5-triazine, 2,4-bis(2,4-dimethylphenyl)-6-(2-hydroxy-4-octyloxyphenyl)-1,3,5-triazine, 2-ethoxy-2'-ethyloxalic acid bisanilide, N-(5-tert-butyl-2-ethoxyphenyl)-N'-(2-ethylphenyl)oxamide, dimethyl(p-methoxybenzylidene)malonate, 2,2'-(1,4-phenylene)bis[3,1-benzoxazin-4-one], N'-(4-ethoxycarbonylphenyl)-N-methyl-N-phenylformamidine, 4-methoxycinnamic acid 2-ethylhexyl ester, 4-methoxycinnamic acid isoamyl ester, 2-phenylbenzimidazole-5-sulfonic acid, 2-cyano-3,3-diphenylacrylic acid 2-ethylhexyl ester, 2-ethylhexyl salicylate, 3-(4-methylbenzylidene)bornan-2-one.

The compositions according to the invention have a viscosity at 20° C. of from 100 to 3000 mPas, preferably from 150 to 2500 mPas, measured at an applied shear force of 30 s$^{-1}$. In general, they are thixotropic, i.e. the viscosity is lowered when the shear force is increased.

By using the compositions according to the invention, the PVC is protected against attack by mold fungi.

Mold fungi of the following genera may be mentioned as examples:
*Alternaria* such as *Alternaria* Lentils,
*Aspergillus* such as *Aspergillus niger*,
*Chaetomium* such as *Chaetomium globosum*,
*Coniophora* such as *Coniophora puetana*,
*Lentinus* such as *Lentinus tigrinus*,
*Penicilliutn* such as *Penicillium glaucum*,
*Polyporus* such as *Polyporus versicolor*,
*Aureobasidium* such as *Aureobasidium pullulans*,
*Sclerophoma* such as *Sclerophoma pityophila*,
*Trichoderma* such as *Trichoderma viridae*.

The compositions according to the invention preferably comprise at least:
a. 2-70% by weight of thiabendazole as active compound
b. 20-97% by weight of one or more plasticizers
c. 0.05-10% by weight of one or more thixotropic agents and optionally
0-40% by weight of one or more further fungicides,
0-30% by weight of one or more epoxides as stabilizers,
and optionally further stabilizers and auxiliaries.

In a particularly preferred embodiment of the invention, the composition comprises at least:
d. 4-50% by weight of thiabendazole as active compound
e. 20-95% by weight of one or more plasticizers
f. 0.05-5% by weight of one or more thixotropic agents
and optionally
0-30% by weight of one or more further fungicides,
0-20% by weight of one or more epoxides as stabilizers,
and optionally further stabilizers and auxiliaries.

The material to be equipped is preferably a polymeric halogen-containing vinyl compound such as, for example, polyvinyl chloride (PVC) and polyvinylidene chloride or a copolymer of vinyl chloride/vinylidene chloride, vinyl chloride/vinyl acetate, vinylidene chloride/vinyl acetate.

The compositions of the polymeric halogen-containing vinyl compounds may also comprise further plastics which act by way of example as polymeric processing aids or impact modifiers. These further plastics are selected from the group consisting of the homo- and copolymers based on ethylene, propylene, butadiene, vinyl acetate, glycidyl acrylate, glycidyl methacrylate, acrylates and methacrylates with alcohol components of branched or unbranched $C_1$-$C_{10}$ alcohols, styrene or acrylonitrile. Particular mention may be made of polyacrylates having identical or different alcohol moieties from the group of the $C_4$-$C_8$ alcohols, in particular of butanol, hexanol, octanol and 2-ethylhexanol, polymethyl methacrylate, methyl methacrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers and methyl methacrylate-styrene-butadiene copolymers.

However, the compositions according to the invention are also suitable for equipping other thermoplastic plastics such as, for example, polyethene (PE), polypropene (PP), polystyrene (PS), polyacrylonitrile (PAN), polyamides (PA), polyesters (PES), polyacrylates or compositions of these.

The compositions according to the invention can be incorporated into the PVC using known methods, for example by extrusion or calendering. Here, the compositions can be either mixed with the auxiliaries (plasticizers, stabilizers, dyes and pigments, fillers, etc.) for PVC production and then incorporated. However, it is also possible to incorporate the compositions into the finished PVC. The appropriate methods are known in the art and are widely employed in industrial production.

The invention also embraces a process for preparing polymeric products from polyvinyl chloride, at least one thixotropic agent, thiabendazole and at least one plasticizer, where the composition according to the invention of at least one thixotropic agent, thiabendazole and at least one plasticizer is incorporated into polyvinyl chloride by extrusion, calendering or compounding.

The invention also embraces a process for preparing the compositions according to the invention where at least one thixotropic agent, thiabendazole and at least one plasticizer are mixed. The mixing process can take place by stirring or grinding, and by all customary compounding processes known to the skilled person from the state of the art. The compositions are preferably mixed by dispersing. Particularly preferably, the compositions are mixed by dispersing and, in a further step, ground using dispersing apparatuses. Appropriate processes and apparatuses such as bead mills or stator/rotor dispersing apparatuses are known to the skilled person from the state of the art, In general, the composition according to the invention comprising thiabendazole, at least one plasticizer and at least one thixotropic agent is employed in an amount of from 0.1 to 10% by weight, preferably 0.2 to 5.0% by weight, based on the polymer to be protected.

In general, the composition according to the invention comprising thiabendazole, at least one plasticizer and at least one thixotropic agent is employed in an amount of from 0.1 to 10% by weight, preferably 0.2 to 5.0% by weight, based on the polyvinyl chloride to be protected.

The invention furthermore embraces polymeric products comprising thermoplastic polymers, thiabendazole, at least one plasticizer and at least one thixotropic agent. In particular, the invention embraces a mixture of polyvinyl chloride, thiabendazole, at least one plasticizer and at least one thixotropic agent.

The mixture according to the invention or the polymeric product of at least one thermoplastic polymer, in particular polyvinyl chloride, thiabendazole, at least one plasticizer and at least one thixotropic agent is further processed according to the known processes. It is used for the production of pipelines, of cables, of wire sheathing, in internal fittings, or in the construction of vehicles or of furniture, in floor coverings, in medical items, in food or drink packing, in gaskets, in tarpaulins, in foils, including composite foils and foils for laminated safety glass, particularly for the vehicle sector and for the architecture sector, or in synthetic leather, toys, packaging containers, adhesive-tape foils, apparel, coatings, or else fibers for textiles.

The composition according to the invention is suitable in particular for preparing mixtures or polymeric products comprising polyvinyl chloride, thiabendazole, at least one plasticizer and at least one thixotropic agent, since the compositions according to the invention have high sedimentation stability and can therefore be employed without further technical treatment in polymers, in particular in polyvinyl chloride. Furthermore, the improved distribution of the active compounds in the polymers allows improved protection against attack or destruction of the polymers by microorganisms.

Accordingly, the invention also embraces the use of the compositions according to the invention for protecting polymers, in particular for protecting polyvinyl chloride, against attack or destruction by microorganisms.

For clarification, it should be mentioned that the scope of the invention encompasses all specified, general or preferred definitions and parameters in any combinations.

EXAMPLES

Material and Abbreviations

Luvotix® R=hydrogenated castor oil CAS No. 8001-78-3 from Lehmann & Voss, Hamburg, Germany
Mesamoll®=alkylsulfonic ester of phenol
DINP=diisononyl phthalate
DIDP=diisodecyl phthalate
ESBO=epoxidized soybean oil CAS No. 8013-07-8; Baerostab LSA, from Baerlocher, Lingen, Germany
BHT=2,6-di-tert-butyl-p-cresol
Ultranox® 668=tris(2,4-di-t-butylphenyl)phosphite Tinivin® 292=composition of bis(1,2,2,6,6-pentamethyl-4-piperidyl)sebacate (CAS No. 4155-26-7) and methyl 1,2,2,6,6-pentamethyl-4-piperidylsebacate (CAS No. 82919-37-7)

Tinuvin® 384-2=benzenepropanoic acid, 3-(2H-benzotriazol-2-yl)-5-(1,1-dimethylethyl)-4-hydroxy-, C7-9-branched and linear alkyl esters (CAS No. 127519-17-9)

Vinnolit S 4170=suspension-PVC for thermoplastic processing from Vinnolit GmbH & Co. KG, Germany Irgastab® CZ 11=PVC stabilizer based on calcium/zinc carboxylate TBZ=thiabendazole OTT=octylisothiazolinone DCOIT=dichlorooctylisothiazolinone

Comparative Example 1

With stirring, 140.4 g of dichlorooctylisothiazolinone (DCOIT) are dissolved in 559.6 g of diisononyl phthalate (DINP). This gives 700 g of a yellow solution having a DCOIT content of 20% (HPLC).

Comparative Example 2

With stirring, 140.0 g of octylisothiazolinone (OIT) are dissolved in 560.0 g of diisononyl phthalate (DINP). This gives 700 g of a light-yellow solution having an OIT content of 20% (HPLC).

Example 3

3 g of Luvotix® R (Lehmann & Voss, Hamburg; hydrogenated castor oil CAS No. 8001-78-3) are dissolved in 87 g of diisodecyl phthalate (DIDP), 210 g of thiabendazole (TBZ) and a further 300 g of DIDP are incorporated at the dissolver and the mixture is stirred at 4000 rpm for 45 min. The liquid pre-dispersion is then ground twice on a ball mill (DYNO-Mühie Multi Lab). This gives a highly thixotropicized dispersion which is, however, processable after stirrring. Active compound content: 35.2% (HPLC).

No sedimentation can be observed after 2 months of storage at 40° C.

Example 4

0.6 g of Luvotix® R (Lehmann & Voss, Hamburg; hydrogenated castor oil CAS No. 8001-78-3) are dissolved in 79.4 g of Mesamoll®, 120 g of thiabendazole (TBZ) and a further 400 g of Mesamoll® are incorporated at the dissolver and the mixture is stirred at 4000 rpm for 45 min. The liquid pre-dispersion is then ground twice on a ball mill (DYNO-Mühle Multi Lab). This gives a thixotropicized dispersion which is, however, readily processable after stirrring. Active compound content: 20.0% (HPLC); viscosity: 1533 mPas/30.1 s No sedimentation is observed after storage at 40° C. for 2 months.

Example 5

2.8 g of Luvotix® R (Lehmann & Voss, Hamburg; hydrogenated castor oil CAS No. 8001-78-3) and 116.62 g of N-octylisothiazolinone are dissolved in 930.58 g of diisononyl phthalate (DINP), 350 g of thiabendazole (TBZ) are incorporated at the dissolver and the mixture is stirred at 4000 rpm for 45 min. The liquid pre-dispersion is then ground twice on a ball mill (DYNO-Mühle Multi Lab). This gives a highly thixotropicized dispersion which is, however, processable after stirrring.

Yield: 1229 g

Viscosity: 1000 mPas (30 l/s)

Content (HPLC): 8.3% N-octylisothiazolinone/25.3% TBZ

<2% sedimentation (clear supernatant based on total fill level) is observed after storage at 40° C. for 2 months.

Example 6

2.8 g of Luvotix® R (Lehmann & Voss, Hamburg; hydrogenated castor oil CAS No. 8001-78-3) and 98 g of N-octylisothiazolinone are dissolved in 1005.2 g of Mesamoll®, 294 g of thiabendazole (TBZ) are incorporated at the dissolver and the mixture is stirred at 4000 rpm for 45 min. The liquid pre-dispersion is then ground twice on a ball mill (DYNO-Milhle Multi Lab). This gives a highly thixotropicized dispersion which is, however, processable after stirrring.

Yield: 1228 g

Viscosity: 1078 mPas (30 Its)

Content (HPLC): 7.0% N-octylisothiazolinone/20.9% TBZ

No sedimentation is observed after storage at 40° C. for 2 months.

Example 7

1.40 g of Luvotix® R (Lehmann & Voss, Hamburg; hydrogenated castor oil CAS No. 8001-78-3), 28.13 g of ESBO (epoxidized soybean oil; CAS No. 8013-07-8) and 27 g of iodopropargyl butylcarbamate (IPBC) are dissolved in 559.13 g of diisononyl phthalate (DINP), 135 g of thiabendazole (TBZ) are incorporated at the dissolver and the mixture is stirred at 4000 rpm for 45 min. The liquid pre-dispersion is then ground twice on a ball mill (DYNO-Mühle Multi Lab). This gives a highly thixotropicized dispersion which is, however, processable after stirrring.

Yield: 602 g

Viscosity: 1000 mPas (30 l/s)

Content (HPLC): 3.5% IPBC/18.4% TBZ

No sedimentation is observed after storage at 40° C. for 2 months.

Example 8

0.75 g of Luvotix® R (Lehmann & Voss, Hamburg; hydrogenated castor oil CAS No. 8001-78-3) 21.0 g of ESBO and 21.6 g of IPBC are dissolved in 1251.6 g of Mesamoll®, 105 g of thiabendazole (TBZ) are incorporated at the dissolver and the mixture is stirred at 4000 rpm for 45 min. The liquid pre-dispersion is then ground twice on a ball mill (DYNO-Mühle Multi Lab). This gives a highly thixotropicized dispersion which is, however, processable after stirrring.

Yield: 1300 g

Viscosity: 270 mPas (30 l/s)

Content (HPLC): 1,5% IPBC/7.7% TBZ

No sedimentation is observed after storage at 40° C. for 2 months.

Example 9

1.13 g of Luvotix® R (Lehmann & Voss, Hamburg; hydrogenated castor oil CAS No. 8001-78-3), 2.25 g of BHT (2,6-di-tert-butyl-p-cresol), 11.25 g of ESBO and 11.25 g of IPBC are dissolved in 667.9 g of Mesamoll®, 56.25 g of thiabendazole (TBZ) are incorporated at the dissolver and the mixture is stirred at 4000 rpm for 45 min. The liquid pre-dispersion is then ground twice on a ball mill (DYNO-Mühle Multi Lab). This gives a highly thixotropicized dispersion which is, however, processable after stirrring.

Yield: 618 g
Viscosity: 243 mPas (30 l/s)
Content (HPLC): 1.48% IPBC/7.7% TBZ

No sedimentation is observed after storage at 40° C. for 2 months.

Example 10

1.5 g of Luvotix® R (Lehmann & Voss, Hamburg; hydrogenated castor oil CAS No. 8001-78-3), 0.75 g of Ultranox 668, 11.25 g of ESBO and 11.25 g of IPBC are dissolved in 669 g of Mesamoll®, 56.25 g of thiabendazole (TBZ) are incorporated at the dissolver and the mixture is stirred at 4000 rpm for 45 min. The liquid pre-dispersion is then ground twice on a ball mill (DYNO-Mühle Multi Lab). This gives a highly thixotropicized dispersion which is, however, processable after stirrring.

Yield: 604 g
Viscosity: 272 mPas (30 l/s)
Content (HPLC): 1.5% IPBC/7.7% TBZ

No sedimentation is observed after storage at 40° C. for 2 months.

Example 11

0.75 g of Luvotix® R (Lehmann & Voss, Hamburg; hydrogenated castor oil CAS No, 8001-78-3), 0.75 g of Tinuvin 292, 11.25 g of ESBO and 11.25 g of IPBC are dissolved in 669.8 g of Mesamoll®, 56.25 g of thiabendazole (TBZ) are incorporated at the dissolver and the mixture is stirred at 4000 rpm for 45 min. The liquid pre-dispersion is then ground twice on a ball mill (DYNO-Mühle Multi Lab). This gives a highly thixotropicized dispersion which is, however, processable after stirrring.

Yield: 618 g
Viscosity: 275 mPas (30 l/s)
Content (HPLC): 1.5% IPBC/7.7% TBZ

No sedimentation is observed after storage at 40° C. for 2 months.

Example 12

0.75 g of Luvotix® R (Lehmann & Voss, Hamburg; hydrogenated castor oil CAS No. 8001-78-3), 0.75 g of Tinuvin 384-2, 11.25 g of ESBO and 11.25 g of IPBC are dissolved in 669.8 g of Mesamoll®, 56.25 g of thiabendazole (TBZ) are incorporated at the dissolver and the mixture is stirred at 4000 rpm for 45 min. The liquid pre-dispersion is then ground twice on a ball mill (DYNO-Mühle Multi Lab). This gives a highly thixotropicized dispersion which is, however, processable after stirrring.

Yield: 615 g
Viscosity: 270 mPas (30 Its)
Content (HPLC): 1.5% IPBC/7.5% TBZ

<2% sedimentation (clear supernatant based on total fill level) is observed after storage at 40° C. for 2 months.

Example 13

479.9 g of Mesamoll are initially charged and Luvotix® R is dissolved with stirring. 60 g of propiconazole (viscous oil) are then added and incorporated at the dissolver at 4000 rpm. 60 g of TBZ are then introduced and dispersed at 4000 rpm for 20 min, and the mixture is then stirred at 3000 rpm for a further 60 min. The liquid pre-dispersion is then ground twice on a ball mill (DYNO-Mühle Multi Lab). This gives a thixotropicized dispersion. Active compound contents:

Yield: 458.6 g
Viscosity: 462.8 mPas (30 l/s)
Content (HPLC): 9.8% propiconazole/9.9% TBZ <2% sedimentation (clear supernatant based on total fill level) is observed after storage at 40° C. for 2 months.

Example 14

50 g of propiconazole are initially charged, 96.5 g of DINP are stirred in at the disperser and 0.5 g of Luvotix® R, 50 g of TBZ and 300 g of further DINP are then added and the mixture is stirred at the dissolver at 4000 rpm for 45 min.

The liquid pre-dispersion is then ground twice on a ball mill (DYNO-Mühle Multi Lab). This gives a highly fluid, slightly thixotropic dispersion.

Viscosity: 323 mPas (30 Vs)
Content (HPLC): 9.9% TBZ/10.0% propiconazole

<2% sedimentation (clear supernatant based on total fill level) is observed after storage at 40° C. for 2 months.

Example 15

Dispersion 1

0.6 g of Luvotix® R is dissolved in 46.3 g of Mesamoll®, 153.1 g of tebuconazole, a further 400 g of Mesamoll® are added and incorporated at the dissolver. The mixture is stirred at 4000 rpm for 45 min.

The liquid pre-dispersion is then passed twice through a ball mill (DYNO-Mühle Multi Lab).

This gives 443 g of a white dispersion.
Viscosity: 2277 mPas/30.1 s
Content (HPLC): 25.2% tebuconazole Dispersion 2

0.6 g of Luvotix® R is dissolved in 79.4 g of Mesamoll®, 120 g of TBZ, a further 400 g of Mesamoll® are added and incorporated at the dissolver. The mixture is stirred at 4000 rpm for 45 min.

The liquid pre-dispersion is then ground twice on a ball mill (DYNO-Mühle Multi Lab).

This gives 414 g of a highly thixotropic, white dispersion
Viscosity: 1533 mPas/30.1 s
Content (HPLC): 20% TBZ 25 g of dispersion 1, 6.25 g of Mesamoll® and 31.25 of dispersion 2 are mixed and homogenized by stirring.

Content (HPLC): 9.9% TBZ/10.0% tebuconazole

No sedimentation is observed after storage at room temperature for 6 months.

Example 16

Dispersion 1

0.6 g of Luvotix® R is dissolved in 69.4 g of DINP, 180 g of TBZ, a further 350 g of DINP are added and incorporated at the dissolver. The mixture is stirred at 4000 rpm for 45 min.

The liquid pre-dispersion is then passed twice through a ball mill (DYNO-Mühle Multi Lab).

This gives 438.2 g of a white, highly thixotropic dispersion.
Viscosity: 3538 mPas/30.1 s
Content (HPLC): 29.8% TBZ

Dispersion 2

0.6 g Luvotix® R is dissolved in 114.8 g DINP, 183.67 g of tebuconazole, a further 300 g of DINP are added and incorporated at the dissolver. The mixture is stirred at 4000 rpm for 45 min.

The liquid pre-dispersion is then passed twice through a ball mill (DYNO-Mühle Multi Lab).

This gives 439 g of a white liquid dispersion.
Viscosity: 2017 mPas/30.1 s
Content (HPLC): 30.1% tebuconazole 30 g of dispersion 1 and 30 g of dispersion 2 are mixed and homogenized by stirring.
Content (HPLC): 15.1% TBZ/14.7% tebuconazole
No sedimentation is observed after storage at room temperature for 6 months.

Example 17

0.6 g of Luvotix® R is mixed with 100 g of Mesamoll®, 100 g of thiabendazole and 20 g of fludioxonil, and a further 379.4 g of Mesamoll® are added and incorporated at the dissolver. The mixture is stirred at 4000 rpm for a further 45 min. The liquid pre-dispersion is then ground twice on a ball mill (DYNO-Mühle Multi Lab). This gives 455 g of a liquid, slightly thixotropic dispersion.
Viscosity: 1103 mPas (30 l/s)
Content (HPLC): 16.6% TBZ, 3.3% fludioxonil
No sedimentation is observed after storage at room temperature 6 months.

Example 18

0.6 g of Luvotix® R is mixed with 100 g of DINP, 125 g of thiabendazole and 25 g of fludioxonil, and a further 349.4 g of DINP are added and incorporated at the dissolver. The mixture is stirred at 4000 rpm for a further 45 min. The liquid pre-dispersion is then ground twice on a ball mill (DYNO-Mühle Multi Lab). This gives 446.8 g of a liquid, slightly thixotropic dispersion.
Viscosity: 769 mPas (30 l/s)
Content (HPLC): 20.9% TBZ, 4.1% fludioxonil
No sedimentation is observed after storage at room temperature for 6 months.

Example 19

0.6 g of Luvotix® R is mixed with 100 g of Mesamoll®, 90 g of thiabendazole and 30 g of fludioxonil, and a further 379.4 g of Mesamoll® are added and incorporated at the dissolver. The mixture is stirred at 4000 rpm for a further 45 min. The liquid pre-dispersion is then ground twice on a ball mill (DYNO-Mühle Multi Lab). This gives 447 g of a liquid, slightly thixotropic dispersion.
Viscosity: 992 mPas (30 l/s)
Content (HPLC): 15.1% TBZ, 4.9% fludioxonil
No sedimentation is observed after storage at room temperature for 6 months.

Example 20

0.6 g of Luvotix® R is mixed with 100 g of DINP, 112.5 g of thiabendazole and 37.5 g of fludioxonil, and a further 349.4 g of DINP are added and incorporated at the dissolver. The mixture is stirred at 4000 rpm for a further 45 min. The liquid pre-dispersion is then ground twice on a ball mill (DYNO-Mühle Multi Lab). This gives 449 g of a liquid, slightly thixotropic dispersion.
Viscosity: 751 mPas (30 l/s)
Content (HPLC): 18.8% TBZ, 6,2% fludioxonil
No sedimentation is observed after storage at room temperature for 6 months.

Example 21

Incorporation of the Dispersions into PVC 100 parts of Vinnolit S 4170
3.0 parts of Irgastab CZ 11
4.0 parts of ESBO (epoxidized soybean oil)
54 parts of DINP (diisononyl phthalate)
X parts of the dispersion according to the invention (see Table 3)

are intensively mixed with one another in a plastic beaker and then homogenized using a calender heated to 180° C. The resulting cooled sheets were then used to prepare 2006× 200×2 mm test specimens.

TABLE 3

(Preparation of the PVC test specimen)

| Ex. No. | Dispersion of Ex. No. used | Parts in the PVC formulation (v.s.) | Total active compound content in ppm |
| --- | --- | --- | --- |
| 21-1 | none | 0 | 0 |
| 21-2 | 1 | 0.81 | 1000 |
| 21-3 | 1 | 0.60 | 750 |
| 21-4 | 2 | 0.81 | 1000 |
| 21-5 | 2 | 0.60 | 750 |
| 21-6 | 13 | 1.64 | 2000 |
| 21-7 | 13 | 1.21 | 1500 |
| 21-8 | 13 | 0.81 | 1000 |
| 21-9 | 14 | 1.61 | 2000 |
| 21-10 | 14 | 1.21 | 1500 |
| 21-11 | 14 | 0.81 | 1000 |
| 21-12 | 15 | 1.61 | 2000 |
| 21-13 | 15 | 1.21 | 1500 |
| 21-14 | 15 | 0.81 | 1000 |
| 21-15 | 16 | 1.61 | 2000 |
| 21-16 | 16 | 1.07 | 1500 |
| 21-17 | 16 | 0.54 | 1000 |
| 21-18 | 7 | 1.43 | 2000 |
| 21-19 | 7 | 1.07 | 1500 |
| 21-20 | 7 | 0.72 | 1000 |
| 21-21 | 17 | 0.81 | 1000 |
| 21-22 | 17 | 1.21 | 1500 |
| 21-23 | 17 | 1.61 | 2000 |
| 21-24 | 18 | 0.64 | 1000 |
| 21-25 | 18 | 0.97 | 1500 |
| 21-26 | 18 | 1.29 | 2000 |
| 21-27 | 19 | 0.81 | 1000 |
| 21-28 | 19 | 1.21 | 1500 |
| 21-29 | 19 | 1.61 | 2000 |
| 21-30 | 20 | 0.64 | 1000 |
| 21-31 | 20 | 0.97 | 1500 |
| 21-32 | 20 | 1.29 | 2000 |
| 21-45 | 6 | 0.58 | 1000 |
| 21-46 | 6 | 0.86 | 1500 |
| 21-47 | 6 | 1.15 | 2000 |
| 21-48 | 5 | 0.48 | 1000 |
| 21-49 | 5 | 0.73 | 1500 |
| 21-50 | 5 | 0.97 | 2000 |

Example 23

Mold Resistance of the PVC Samples

Following ISO 846, the samples were assessed for their biological activity.

The PVC specimens from Example 26 are in each case cut into 2×2 cm pieces, one test specimen is aged in running water for 120 h, the other one is tested without any prior treatment.

The test specimens are placed on a malt agar (in Petri dishes) contaminated with a mixed spore suspension of *Penicillium funicolosum* (ATCC 36839), *Chaetomium glohosum* (ATCC 6205), *Trichoderma longibrachiaturn* (ATCC 9645), *Paecilomyces variotii* (ATCC 18502) and *Aspergilius niger* (ATCC 6275) and incubated at 26° C. and 80% rel. atmospheric humidity for two weeks.

The fungal growth on the agar plates is then examined with a stereo magnifying glass and assessed in accordance with the following scheme:

TABLE 4

(Assessment scheme)

| Assessment | Description |
|---|---|
| 0 | insufficient mold resistance<br>sample >10% overgrown |
| 1 | moderate mold resistance<br>sample at most 10% overgrown |
| 2 | good mold resistance<br>sample not overgrown, or only at the edge, no zone of inhibition around the test specimen |
| 3 | very good mold resistance<br>sample not overgrown, there is a zone of inhibition around the test specimen |

For the samples tested, the following assessments were obtained:

TABLE 5

(Biological assessment of mold resistance)

| Sample of Ex. No. | Assessment without watering | Assessment after watering (120 h) | Total active compound content in ppm |
|---|---|---|---|
| 21-1 (Zero sample) | 0 | 0 | 0 |
| 21-2 (Comparison 1) | 0 | 0 | 1000 |
| 21-3 (Comparison 1) | 0 | 0 | 750 |
| 21-4 (Comparison 2) | 1-2 | 0-1 | 1000 |
| 21-9 | 2 | 2 | 2000 |
| 21-10 | 2 | 2 | 1500 |
| 21-11 | 2 | 2 | 1000 |
| 21-17 | 2 | 2 | 1000 |
| 21-20 | 3 | 3 | 1000 |
| 21-24 | 2 | 2 | 1000 |
| 21-25 | 2 | 2 | 1500 |
| 21-26 | 2 | 2 | 2000 |
| 21-30 | 2 | 2 | 1000 |
| 21-31 | 2 | 2 | 1500 |
| 21-32 | 2 | 2 | 2000 |
| 21-48 | 2 | 2 | 1000 |
| 21-49 | 2 | 2 | 1500 |
| 21-50 | 2 | 2 | 2000 |

What is claimed is:

1. A fungicidal composition for anti-fungal growth in polymers, the fungicidal composition comprising:
   a fungicide for inhibiting growth of fungi in polymers, the fungicide comprising thiabendazole, salts of thiabendazole or acid addition compounds of thiabendazole;
   a plasticizer; and
   a thixotropic agent.

2. The composition as claimed in claim 1, further comprising an iodine-containing fungicide and an epoxide.

3. The composition as claimed in claim 2, wherein the iodine-containing fungicide is 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl)hexyldicarbamate, 3-iodo-2-propynyloxyethanol ethylcarbamate, 3-iodo-2-propynyloxyethanol phenylcarbamate, 3-iodo-2-propynylthioxo thioethylcarbamate, 3-iodo-2-propynyl carbamate (IPC), 3-bromo-2,3-diiodo-2-propenyl ethylcarbamate, 3-iodo-2-propynyl n-hexy/carbamate, 3-iodo-2-propynyl cyclohexylcarbamate or diiodomethyl-p-tolylsulfone.

4. The composition as claimed in claim 2 or 3, wherein the epoxide is selected from the group consisting of linseed oil epoxidates, vernonia oil epoxidates, sunflower oil epoxidates and soybean oil epoxidates.

5. The composition as claimed in claim 2, further comprising a stabilizer selected from the group consisting of the sterically hindered amines and phenols, esters of β-(3,5-di-tert-butyl-4-hydroxy-phenyl)propionic acid with mono- or polyhydric alcohols, esters of B-(5-tert-butyl-4-hydroxy-3-methylphenyl)propionic acid with mono- or polyhydric alcohols, phosphites, phosphonates, UV absorbers, secondary arylamines, lactones, benzofuranones, thioethers and thioesters.

6. The composition as claimed in claim 1, wherein the thixotropic agent is selected from the group consisting of fumed silica or precipitated silica, hydrogenated castor oil, sulfated castor oil or polyamide waxes.

7. The composition as claimed in claim 1, further comprising at least one further fungicide selected from the group consisting of azaconazole, bromuconazole, cyproconazole, dichlobutrazole, diniconazole, difenconazole, hexaconazole, metaconazole, penconazole, propiconazole, tebuconazole, azoxystrobin, fludioxonil, dichlofluanid, tolylfluanid, fluorfolpet, methfuroxam, carboxin, fenpiclonil, butenafin, imazalii, N-octylisothiazolin-3-one, dichloro-N-octylisothiazolinone, mercaptobenzothiazole, thiocyanatomethylthiobenzothiazole, N-butyl-bentisothiazolinone, 1-hydroxy-2-pyridinthione and their Cu, Na, Fe, Mn, Zn salts, tetrachloro-4-methylsulfonylpyridine, 3-iodo-2-propynyl n-butylcarbamate, diiodomethyl-p-tolylsulfone, bethoxazin, 2,4,5,6-tetrachloroisophthalodinitrile and carbendazim.

8. The composition as claimed in claim 1, wherein the composition comprises at least 2-70% by weight of the thiabendazole, 20-97% by weight of the plasticizer and 0.05-10% by weight of the thixotropic agent.

9. The composition as claimed in claim 1, wherein the plasticizer is at least one epoxidized fatty acid glyceride, epoxidized fatty acid ester or epoxidized fatty acid or a mixture of these compounds.

10. A polymeric product comprising a thermoplastic polymer and a composition as claimed in claim 1.

11. The polymeric product as claimed in claim 10, wherein the thermoplastic polymer is polyvinyl chloride.

12. A process for preparing the polymeric product as claimed in claim 10 or 11, the process comprising mixing a composition comprising: thiabendazole, salts of thiabendazole or add addition compounds of thiabendazole; a plasticizer; and a thixotropic agent with the thermoplastic polymer.

13. A method for protecting polymeric products based on thermoplastic polymers against attack and destruction by microorganisms, the method comprising in the composition as claimed in claim 1 in the thermoplastic polymers for preparing the polymeric products.

14. A fungicidal composition comprising:
a biocidal chemical compound;
a plasticizer; and
a thixotropic agent,
wherein the biocidal chemical compound consists of fungicide, and the fungicide comprises thiabendazole, salts of thiabendazole or add addition compounds of thiabendazole.

15. A fungicidal composition comprising:
thiabendazole, salts of thiabendazole or add addition compounds of thiabendazole;
a plasticizer comprising at least one of epoxidized fatty adds, epoxidized fatty add glyceride, and epoxidized fatty acid ester; and
a thixotropic agent.

16. The fungicidal composition according to claim 15, wherein the plasticizer comprises epoxidized fatty acids.

17. The fungicidal composition according to claim 16, wherein the epxidized fatty acids comprise fatty acid oil epoxidates.

18. The fungicidal composition according to claim 17, wherein the fatty acid oil epoxidates are selected from the group consisting of linseed oil epoxidates, vernonia oil epoxidates, sunflower oil epoxidates, and soybean oil epoxidates.

* * * * *